United States Patent [19]

Chen et al.

[11] Patent Number: 4,879,390

[45] Date of Patent: Nov. 7, 1989

[54] DELTA-BUTYROLACTAMS, THEREOF, PROCESSES FOR THE PREPARATION THEREOF AND THEIR MEDICAL USE

[75] Inventors: Yen-rong Chen; Ming-he Yang; Liang Huang; Geng-tao Liu, all of Beijing, China; Ulrich Benz, Duesseldorf, Fed. Rep. of Germany

[73] Assignees: Chinese Academy of Medical Sciences, Beijing, China; Bayer Aktiengesellschaft, Leverkusen, Fed. Rep. of Germany

[21] Appl. No.: 186,540

[22] Filed: Apr. 27, 1988

Related U.S. Application Data

[63] Continuation of Ser. No. 769,097, Aug. 26, 1985, abandoned.

[30] Foreign Application Priority Data

Aug. 24, 1984 [DE] Fed. Rep. of Germany ....... 3431257

[51] Int. Cl.$^4$ ................ C07D 207/38; C07D 491/08
[52] U.S. Cl. ..................................... 548/453; 548/544
[58] Field of Search ............................... 548/453, 544

[56] References Cited

PUBLICATIONS

Johns et al., Aust. J. Chem., vol. 20, 1967, pp. 2795, 2796 and 2797.
Shoet et al., Journal of the Chemical Society, Chemical Communications, No. 7, Apr. 5, 1978, pp. 281-282.

Primary Examiner—David B. Springer
Attorney, Agent, or Firm—Sprung Horn Kramer & Woods

[57] ABSTRACT

Purified Clausenamide of the formula

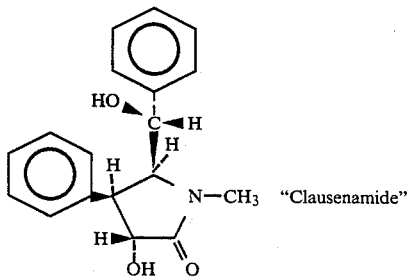

is obtained by extraction of leaves of *Clausena lansium* followed by purification, Reduction products, ethers, etc. can be produced. The compounds are effective in treating hypoxia and amnesia.

9 Claims, No Drawings

DELTA-BUTYROLACTAMS, THEREOF, PROCESSES FOR THE PREPARATION THEREOF AND THEIR MEDICAL USE

This is a continuation of application Ser. No. 769,097, filed Aug. 26, 1985, now abandoned.

The present invention relates to a new pharmacologically active phenyl- and benzyl-substituted δ-butyrolactam (which is hereinafter called "Clausenamide"), its isolation from plants of the Rutaceae Clausena species, certain derivatives of Clausenamide and their use as hypoxiaprotective and antiamnestic agents. The invention is also concerned with pharmaceutical compositions containing Clausenamide or its derivatives and with their manufacture.

Rutaceae *Clausena anicata* was reported to be used as a folk medicine in certain parts of Africa (I. Mester et al., Planta Medica 32 (1) 81, 1977). It has also been reported that the crude extract of *Clausena indica* Oliv. has cardiovascular activity and that two coumarin derivatives, Clausmarins A and B, isolated from *Clausena pentaphalla* (Roxb.) DC have spasmolytic activity (Dhan Prakash et al., Phytochem. 17, 1194, 1978; Aboo Shoeb et al., J.C.S. Chem. Commun. 281, 1978). About fifty constituents have already been isolated from the roots, stems, etc. of various species of Clausena. Most of these constituents are derivatives of coumarin, carbazole and terpene; so far only two linear carboxylic acid amides were reported to be present in the leaves of Clausena plants (S. R. Johns et al., Aust. J. Chem. 20, 2795, 1967; Dhan Prakash et al., Indian J. Chem. Sect. B 19B (12), 1975).

It has now been found that the leaves of *Clausena lansium* contain a δ-butyrolactam which contains a phenyl and a benzyl substituent in two stereoisomeric forms ("Clausenamide" and "Compound (9)") and a structurally closely related bicyclic butyrolactam. Clausenamide and its derivatives were found to have various valuable pharmacological properties. The structure of these compounds has been confirmed by chemical derivatisation and by spectral data.

The present invention is directed to compounds of the general formula (I):

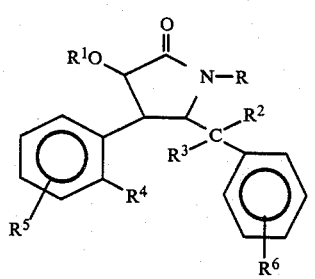

(I)

wherein

R is an alkyl, aryl or aralkyl group having from 1 to 10 carbon atoms;

$R^1$ represents hydrogen, an alkyl, aryl or aralkyl group having from 1 to 10 carbon atoms, an acyl group having from 1 to 18 carbon atoms or together with $R^3$ represents a chemical bond;

$R^2$ represents hydrogen or together with $R^3$ represents oxygen;

$R^3$ represents hydrogen, hydroxy, an alkoxy, aryloxy or aralkyloxy group having from 1 to 10 carbon atoms, an acyloxy group having from 1 to 18 carbon atoms, together with $R^1$ or $R^4$ represents a chemical bond or together with $R^2$ represents oxygen;

$R^4$ is hydrogen, together with $R^3$ represents a chemical bond or has the meaning of $R^5$; and $R^5$ and $R^6$ which are the same or different, represent hydrogen, an alkyl, aryl or aralkyl group having from 1 to 10 carbon atoms, an alkoxy, aryloxy or aralkoxy group having from 1 to 10 carbon atoms, an acyl group having from 1 to 18 carbon atoms, $CF_3$, $OCF_3$, nitro, hydroxy, halogen, amino, dialkylamino having from 1 to 4 carbon atoms in the alkyl groups, carboxy, $SO_3H$ or acylamino having 1 to 18 carbon atoms.

In the above definitions, "alkyl" and "alkoxy" groups preferably contain 1 to 6 carbon atoms and in particular mean methyl or methoxy; "aryl", "aralkyl", "aryloxy" and "aralkyloxy" preferably mean phenyl, benzyl, phenoxy and benzyloxy, respectively, and "acyl" groups preferably contain 1 to 4 carbon atoms and in particular mean acetyl groups. Preferred compounds according to general formula (I) are those
wherein
R represents methyl;
$R^1$ is hydrogen, alkyl, acyl or together with $R^3$ represents a chemical bond;
$R^2$ is hydrogen;
$R^3$ represents hydroxy, alkyloxy, acyloxy or together with $R^1$ or $R^4$ represents a chemical bond and
$R^5$ and $R^6$ are hydrogen.

The aforementioned compounds which can be isolated from leaves of *Clausena lansium* have the following structural formulae:

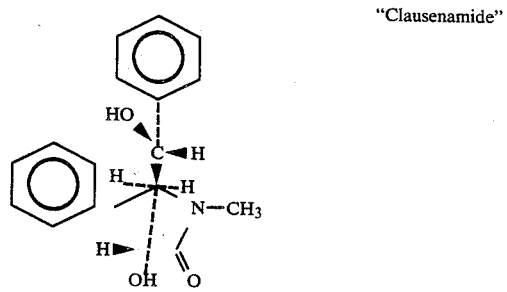

"Clausenamide"

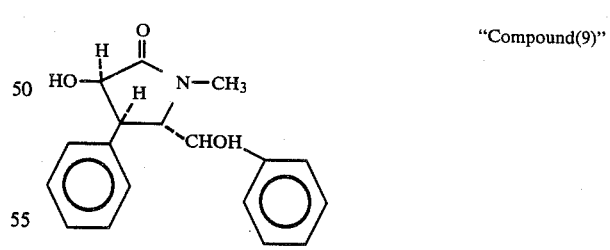

"Compound(9)"

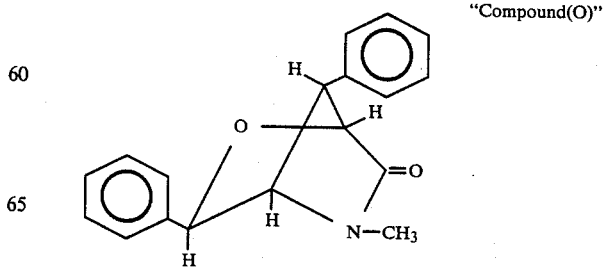

"Compound(0)"

(The stereochemistry was confirmed by X-ray crystal diffraction).

The present invention is also directed to the isolation of Clausenamide by a method which comprises the steps of:
(a) treating leaves of Clausena lansium with boiling water,
(b) mixing the concentrated aqueous extract with an adsorbent (e.g. silica gel, aluminium oxide, sand, cellite, cellulose or polyamide),
(c) extracting the adsorbent with an organic solvent such as chloroform, ethyl acetate, ether, methylene chloride and ethylene chloride, preferably chloroform,
(d) concentrating the organic eluate and
(e) washing the concentrate with a cold $C_1$–$C_6$-alcohol or $C_2$–$C_6$-Ketone (e.g. methanol).

Furthermore the invention is directed to the isolation of Compound (O) by a method which comprises the steps of:
(a) treating leaves of Clausena lansium with boiling water,
(b) adding dilute acid (e.g. HCl) to the concentrated aqueous extract,
(c) passing the supernatant through a cation ion exchange resin, preferably in its $H^+$-form,
(d) treating the resin with a base, preferably aqueous ammonia,
(e) extracting the resin with an organic solvent such as ethers, chloroform, methylene chloride, acetic acid esters of $C_1$–$C_6$ alcohols or $C_2$–$C_6$ ketones, preferably with diethyl ether,
(f) chromatographing the concentrated extract on silica or aluminium oxide with chloroform, methylene chloride, ether or chloroform/methanol mixture as eluting agent and
(g) collecting and concentrating the eluate with an Rf-value corresponding to "Compound (O)" (0.80 in the case of silica gel and chloroform as eluting agent).

The instant invention is also directed to the isolation of Compound (9) by a method which comprises the steps of
(a) treating leaves of Clausena lansium with boiling water,
(b) evaporating water from the extract and dissolving the residue in dilute acid (e.g. HCl),
(c) passing the supernatant through a cation exchange resin, preferably in its $H^+$-form,
(d) treating the resin with base, e.g. aqueous ammonia,
(e) extracting the resin with an organic solvent such as ethers, chloroform, methylene chloride, acetic acid esters of $C_1$–$C_6$-alcohols or $C_2$–$C_6$-ketones,
(f) chromatographing the concentrated extract on $SiO_2$ or $Al_2O_3$ and eluting with chloroform, methylene chloride, ether or chloroform/methanol mixture and
(g) collecting and concentrating the eluate (e.g. monitored by TLC) corresponding to "Compound (9)" ($R_f$-value of 0.20 in the case of silica gel and chloroform as eluting agent).

It is preferred to recrystallize the crude products obtained by the above isolation methods from alcohols, e.g. methanol or ethanol.

Derivatives of Clausenamide, Compound (9) and Compound (O) according to the general formula (I) may be synthesized by reduction (e.g. catalytic hydrogenation), oxidation (e.g. by chromic oxide), esterification and etherification methods known per se.

The present invention also relates to pharmaceutical compositions and medicaments containing compounds of formula (I) as an active ingredient and to the manufacture of these compositions.

The invention is also directed to the use of compounds of formula (I) for the treatment of hypoxia and amnesia.

The compounds of formula (I) in animal experiments had a pronounced cerebral hypoxia protective and antiamnestic effect which is significantly stronger than that of piracetam which is the structurally most closely related compound in the area of cerebral therapeutics and nootropics.

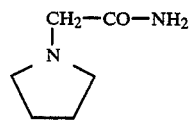
Piracetam

Even at high doses the animals did not show any significant changes in their behaviour. The hypoxia protective effect apparently is not caused by an unspecific sedation, therefore, which would give rise to a reduced need for oxygen. The acute toxicity of the compounds of the formula (I) was found to be very low.

The pharmaceutical compositions according to the invention may for example take the form of ointments, gels, pastes, creams, sprays (including aerosols), lotions, suspensions, solutions and emulsions of the active ingredient in aqueous or non-aqueous diluents, syrups, granules or powders.

The compositions are preferably in the form of a sterile isotonic aqueous solution or in the form of tablets, capsules, pills and suppositories comprising a compound of the invention either alone or in admixture with a diluent.

The diluents to be used in pharmaceutical compositions (e.g. granulates) adapted to be formed into tablets, dragees, capsules and pills include the following:
(a) fillers, e.g. starch, sugars, and silicic acid;
(b) binding agents, e.g. cellulose derivatives, alginates, gelatine and polyvinyl pyrrolidone;
(c) moisturizing agents, e.g. glycerol;
(d) disintegrating agents, e.g. agar-agar, calcium carbonate and sodium bicarbonate;
(e) resorption accelerators, e.g. quarternary ammonium compounds;
(f) surface active agents, e.g. cetyl alcohol;
(g) adsorptive carriers, e.g. kaolin and bentonite;
(h) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The production of the above-mentioned pharmaceutical compositions and medicaments is carried out by any method known in the art, for example by mixing the active ingredient(s) with the diluent(s) to form a pharmaceutical composition (e.g. a granulate) and then forming the composition into the medicament (e.g. tablets).

The pharmaceutical compositions according to the invention preferably contain about 0.1 to 99.5, more preferably from about 0.5 to 95% of the active ingredient by weight of the total composition.

The preferred daily dose for administration of the medicaments of the invention is 0.001 mg to 0.2 mg of the active ingredient.

The following Examples illustrate the invention.

EXAMPLE 1

Isolation of Clausenamide

Eighty kg of dried leaves of *Clausena lansium* (lour) Skeels were first boiled with water. The aqeuous extract was concentrated to give 18 kg of crude syrup. The crude syrup was mixed with silica gel and extracted with chloroform. The chloroform extract was concentrated to give a brown syrup, which was washed with cold methanol. The yellowish powder thus obtained was recrystallized from methanol to give white needles of Clausenamide.

Clausenamide: white needles, m.p. 239°–40° C. $[\alpha]_D^{21}$ 0.00 (0.53 in MeOH), molecular formula $C_{18}H_{19}NO_3$ based on the elementary analysis and high resolution MS ($M^+$: 297.1364), soluble in hot methanol, DMSO and DMF, only slightly soluble in common organic solvents such as $CHCL_3$ $CH_2Cl_2$, ether, ethyl acetate, etc.

$IR\gamma_{max}^{KBr}$ cm$^{-1}$: 3400, 3310(OH), 1680(amide), 1600, 1580, 1490, 1450, 740, 690(monosubstituted benzene rings).

$UV\lambda_{max}^{MeOH}$ nm(lgε): 257(2.70).

High resolution MS m/z: 297.1364($M^+$, $C_{18}H_{19}NO_3$), 298.1448 ($C_{18}H_{20}NO_3$), 191.0946($C_{11}H_{13}NO_2$), 190.0881 ($C_{11}H_{12}NO_2$), 174.0912($C_{11}H_{12}NO$), 162.0924($C_{10}H_{12}NO$), 144.0815($C_{10}H_{10}N$), 134.0687($C_9H_{10}O$), 133.0646($C_9H_9O$). Elementary analysis found: C=72.39, H=6.39, N=4.51.

TABLE 1

$^1$H—NMR; chemical shift and assignment for Clausenamide

| ppm | Hydrogen |
|---|---|
| 3.05 (s; 3H) | N—CH$_3$ |
| 3.50 (dd, J = 10,8; 1H) | C$_4$—H |
| 3.90 (d, J = 10; 1H) | C$_3$—H |
| 4.30 (dd, J = 8,2; 1H) | C$_5$—H |
| 4.65 (d, J = 2; 1H) | C$_7$—H |
| 4.70–5.40 (m; 2H) | OH |
| 6.50–6.70 (m; 2H) | aromatic H |
| 6.90–7.30 (m; 8H) | aromatic H |

$^{13}$C-NMR data are given below in Table 9.

The chemical structure of Clausenamide was also confirmed by X-ray diffraction data.

EXAMPLE 2

Isolation of Compound (O) and Compound (9)

80 kg of dried leaves of *Clausena lansium* (Lour) Skeels were boiled with water. The aqueous extract was concentrated to give 18 kg of crude syrup. 16 kg of the crude syrup were treated with 0.06N HCl (80 l) and the supernatant was passed through a column of wet H$^\pm$ form cation ion exchange resin (from 48 kg of Na$^\pm$form cation ion exchange resin). The resin was then washed with deionized water, treated with 2% aqueous NH$_4$OH (32.2 l) and finally extracted with diethyl ether (60 l). The chloroform solution of the concentrated ether extract was treated repeatedly on silica gel columns (ratio varied from 100:1 to 20:1) with chloroform as eluting agent. The eluates at $R_f$=0.80 (Compound (O)) and at $R_f$=0.20 (Compound (9)) were collected and concentrated. The crystals thus obtained were recrystallized from methanol. 0.18 g of white prism crystals, m.p. 164°-6° C., (Compound (O)) and 3.31 g of white cubes, m.p. 205°–6° C. (Compound (9)) were obtained.

Compound (O): $[\alpha]_D^{24.5} = -40°$ (0.225 in MeOH).

| Elementary analysis | | |
|---|---|---|
| | calculated (for $C_{18}H_{17}NO_2$) | found |
| C | 77,42 | 77,06 |
| H | 6,09 | 6,13 |
| N | 5,02 | 4,76 |

High resolution MS: ($M^+$ +1)=280,1371

$IR\gamma_{max}^{KBr}$ cm$^{-1}$: 1690 (amide-carbonyl), 3080, 3060, 3010, 1600, 1500, 750, 730, 705, 700.

$UV\lambda_{max}^{MeOH}$ nm (lgε): 209 (4.35), 257 (2.60).

TABLE 2

$^1$H—NMR (in CDCl$_3$); chemical shift and assignment for Compound (0)

| ppm | Hydrogen |
|---|---|
| 2,95 (s; 3H) | N—CH$_3$ |
| 3,60 (s; 1H) | C$_4$—H |
| 4,09 (s; 1H) | C$_5$—H |
| 4,81 (s; 1H) | C$_3$—H |
| 5,00 (s; 1H | C$_7$—H |
| 7,10–7,50 (m; 10H) | aromatic H |

$^{13}$C-NMR data are given below in Table 9.

Compound (9): $[\alpha]_D^{19}$=0.00 (0.29 in MeOH).

| Elementary analysis: | | |
|---|---|---|
| | calculated (for $C_{18}H_{19}NO_3$) | found |
| C | 72,76 | 73,00 |
| H | 6,45 | 6,46 |
| N | 4,72 | 4,50 |

High resolutions MS: ($M^+$ +1)=298,1453 ($C_{18}H_{20}NO_3$).

$IR\gamma_{max}^{KBr}$ cm$^{-1}$: 3440, 3340 (OH), 1660 (amide-carbonyl), 3060, 3030, 1600, 1490, 750, 770 (monosubstituted benzene).

$UV\lambda_{max}^{MeOH}$ nm (lgε): 258 (2.59).

TABLE 3

$^1$H—NMR (in DMSO); chemical shift and assignment

| ppm | Hydrogen |
|---|---|
| 2,90 (S; 3H) | N—CH$_3$ |
| 3,07 (t; J = 7; 1H) | C$_4$—H |
| 3,89 (m; 2H) | C$_3$—H; C$_5$—H |
| 5,00 (dd, J = 5,3; 1H) | C$_7$—H |
| 5,53 (d, J = 7; 1H) | C$_3$—OH; disappeared on addition of D$_2$O |
| 5,73 (d, J = 5; 1H) | C$_7$—OH; disappeared on addition of D$_2$O |
| 6,75–6,93 (m; 2H) | aromatic H |
| 6,95–7,33 (m; 8H) | aromatic H |

¹³C-NMR data are given below in Table 9.

EXAMPLE 3

Synthesis of derivatives of Clausenamide having the general formula

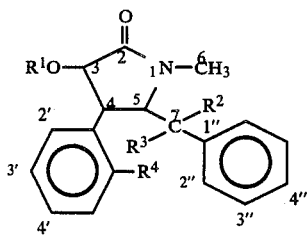

(The stereochemistry is the same as given above for Clausenamide itself).

(a) Compound (I): $R^1 = CH_3CO-$; $R^2 = CH_3COO-$; $R^3 = R^4 = H$ 600 mg of Clausenamide were dissolved in 10 ml of a mixture of anhydrous pyridine and acetic anhydride (1:1). After the reaction mixture had been stirred at room temperature for 24 hrs., it was poured into 30 ml of ice water and extracted three times with diethyl ether. The ether extract was washed subsequently with 2% HCl (15 ml) and water (25 ml, 20 ml, 15 ml). It was dried with $Na_2SO_4$ and solvent was removed to give 750 mg of a transparent syrup. The crude reaction product was recrystallized from methanol to yield 570 mg of white cubes, m.p. 165°-7° C.

| Elementary analysis: | | |
|---|---|---|
| | Calculated for $C_{22}H_{23}NO_5$ | found |
| C | 69,29 | 69,12 |
| H | 6,04 | 6,04 |
| N | 3,67 | 3,68 |

IR$\gamma_{max}^{KBr}$ cm$^{-1}$: 1735 (ester-carbonyl), 1715 (shoulder, estercarbonyl), 1700 (amide-carbonyl), 1215 (C—O).

MS m/z (%): 382 (M$^+$+1; 0,5), 261 (0,3), 232(17), 172(100), 144(9), 91(8), 43(40).

TABLE 4

| ¹H—NMR (in CDCl₃); chemical shift and assignment | |
|---|---|
| ppm | Hydrogen |
| 1,88 (s; 3H) | CH₃COO |
| 1,98 (s; 3H) | CH₃COO |
| 2,59 (s; 3H) | N—CH₃ |
| 4,07 (dd, J = 10,8; 1H) | C₄—H |
| 4,43 (dd, J = 8,2 ; 1H) | C₅—H |
| 5,72 (d, J = 10; 1H) | C₃—H |
| 5,74 (d, J = 2; 1H) | C₇—H |
| 6,08-7,50 (m; 10H) | aromatic H |

(b) Compound (IV): $R^1 = CH_3CO-$; $R^2 = R^3 = R^4 = H$ 500 mg of Compound (I) in 40 ml of methanol were hydrogenated in the presence of 200 mg of Pd/C under 20 atm. at 40° C. for 7.5 hrs. After removal of the catalyst, the solvent was taken off to give 464 mg of a transparent syrup. It was chromatographed on $SiO_2$ to give compound (IV) in amorphous form with Rf 0.58 on TLC ($SiO_2$ plate, developing solvent: benzene/methanol 95:5).

IR$\gamma_{max}^{film}$ cm$^{-1}$: 1740 (ester-carbonyl), 1710 (amide-carbonyl), 1203 (C—O).

TABLE 5

| ¹H—NMR (in CDCl₃); chemical shift and assignment | |
|---|---|
| ppm | Hydrogen |
| 2,10 (s; 3H) | CH₃COO |
| 2,49 (dd, J = 2,8; 2H) | C₇—H |
| 2,56 (s; 3H) | N—CH₃ |
| 3,78-4,18 (m; 2H) | C₄—H, C₅—H |
| 6,03 (d, J = 10; 1H) | C₃—H |
| 6,78-7,00 (m; 2H) | aromatic H |
| 7,11-7,51 (m; 8H) | aromatic H |

MS m/Z (%): 324 (M+1; 37), 264(M-60; 4), 232(M-91; 39), 172(M-60-91; 100), 91 (39).

(c) Compound (V): $R^1 = R^2 = R^3 = R^4 = H$ 50 mg of Compound (IV) in 2 ml of 2% KOH-MeOH were heated on a water bath for 50 min. Two ml of water, 5 ml of chloroform and 2 ml of methanol were added. The chloroform layer was separated, dried with $Na_2SO_4$ and concentrated to give a transparent syrup, which was crystallized by adding ether. White granular crystals of m.p. 123°-5° C. were obtained.

IR $\gamma_{max}^{KBr}$ cm$^{-1}$: 3290 (OH), 1680 (amide-carbonyl).

MS m/Z(%): 282 (M+1; 5), 190

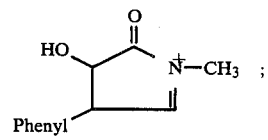

100), 162 (190-CO; 38), 134 (47), 91(42).

(d) Compound (VI): $R^1 = R^4 = H$; $R^2 + R^3 = O$ 1,5 g of Clausenamide in 20 ml of pyridine were oxidized with 30 ml of Conforth's reagent, which was prepared by adding a solution of 3 g of $CrO_3$ in 3 ml of $H_2O$ to 27 ml of ice cooled pyridine. The mixture was left overnight and then poured into 100 ml of water and extracted with diethyl ether. The ether solution was washed twice with water and dried with $Na_2SO_4$. After removal of the solvent, the residue left was recrystallized with methanol. White prisms of m.p. 207°-10° C. were obtained.

$[\alpha]_D^{25} = 0.00$ (0.26 in $CHCl_3$).

IR $\gamma_{max}^{KBr}$ cm$^{-1}$: 3260 (OH), 1690 (aromatic ketone), 1670 (amide-carbonyl), 3060, 3040, 1600, 1500.

UV $\lambda_{max}^{MeOH}$ nm(lg $\epsilon$): 205(4.31), 252 (4.07).

MS m/Z (%): 295 (M$^+$; 1), 190

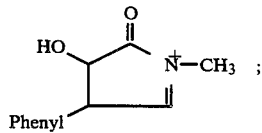

100), 162(190—CO; 45), 134 (70), 133(40), 105(35), 91(20), 77(50).

TABLE 6

| ¹H—NMR in CDCl₃; chemical shift and assignment | |
|---|---|
| ppm | Hydrogen |
| 2,01 (br; 1H) | OH |
| 2,92 (s; 3H) | N—CH₃ |
| 3,86 (t, J = 8; 1H) | C₄—H |
| 4,95 (d, J = 8; 1H) | • C₅—H |

TABLE 6-continued

| ¹H—NMR in CDCl₃; chemical shift and assignment | |
|---|---|
| ppm | Hydrogen |
| 5,40 (d, J = 8; 1H) | C₃—H |

(e) Compound (VII): $R^1=R^2=H$; $R^3+R^4=$chemical bond 150 mg of Clausenamide were hydrolyzed in 30 ml of 6N HCl in a sealed tube at 105° C. for 24 hrs. At the end white flakes appeared in the solution. The mixture was filtered and the filtrate was extracted 3 times with ether (60 ml, 50 ml and 40 ml). The ether extracts were combined and washed once with water. After being dried, the ether was driven off to yield a transparent syrup which crystallized in ether. The crude reaction product was recrystalized from ether. White needles of m.p. 188°-90° C. were obtained.

High resolution MS: 279,1176 (calculated for $C_{18}H_{17}NO_2$: 279, 1259).

MS m/Z (%): 279 (M+, 100).

IR $\gamma_{max}^{KBr}$ cm⁻¹: 3300 (OH), 1680(amide-carbonyl), 1600, 1490, 768, 750, 710.

UV $\lambda_{max}^{MeOH}$ nm (lg ε): 220 (3.60), 263 (2.90).

TABLE 7

| ¹H—NMR in CDCl₃; chemical shift and assignment | |
|---|---|
| ppm | Hydrogen |
| 2,57 (s; 1H) | OH (disappeared on addition of D₂O) |
| 2,96 (s; 3H) | N—CH₃ |
| 3,99 (m; 1H) | |
| 4,36 (m; 3H) | |
| 6,90-7,55 (m; 9H) | aromatic H |

¹³C-NMR data are given below in Table 9.

(f) Compound (VIII): $R^1=CH_3CO—$; $R^2=H$; $R^3+R^4=$chemical bond 15 mg of Compound (VII) were dissolved in 1.5 ml of acetic anhydride/pyridine (1:). The mixture was left at room temperature for two days. Then the volatile components were removed under reduced pressure. The residue was dissolved in 3 ml of chloroform. The chloroform solution was washed with 2 ml of 10% NH₄OH followed by three times 2 ml of water and the solvent was driven off. A white amorphous solid of m.p. 148°-51° C. was obtained.

IR $\gamma_{max}^{film}$ cm⁻¹: 1745 (ester-carbonyl), 1710(amide-carbonyl), 1230(C—O), 3060, 3030, 1600, 1500, 750, 720, 700.

MS m/Z(%): 321 (M+; 5), 279(30), 261 (M—CH₃COO; 100).

TABLE 8

| ¹H—NMR in CDCl₃; chemical shift and assignment | |
|---|---|
| ppm | Hydrogen |
| 2,22 (s; 3H) | CH₃COOH |
| 3,09 (s; 3H) | N—CH₃ |
| 4,00 (dd, J = 7,2; 1H) | C₅—H |
| 4,34 (dd, J = 7,3; 1H) | C₄—H |
| 4,51 (d, J = 2; 1H) | C₇—H |
| 5,30 (d, J = 3; 1H) | C₃—H |
| 7,00-7,80 (m; 9H) | aromatic H |

EXAMPLE 4

Synthesis of Derivatives of Compound (9)

(a) A solution of 150 mg of Compound (9) in 8 ml of acetic anhydrid and pyridine (1:1) was stirred at room temperature for two days. The reaction mixture was poured into water and extracted with chloroform. The residue left after removal of chloroform was recrystallized with methanol. 135 g of acetate with m.p. 125°-6° C. was obtained in cubic crystalline form.

(b) 150 mg of compound (9) in two ml of pyridine were oxidized with 3 ml of Conforth's reagent, which was prepared by adding a solution of 0.3 g of CrO₃ in 0.3 ml of H₂O to 2.7 ml of ice cooled pyridine. The mixture was left overnight and then poured into 10 ml of water and extracted with diethyl ether. The ether solution was washed three times with water and dried with Na₂SO₄. After removal of the solvent, the residue left was recrystallized with methanol to give 57 mg of a crystalline solid, m.p. 202°-5° C.

TABLE 9

| ¹³C—NMR in CDCl₃; Chemical Shift and Assignment for Clausenamide, (VII), Compound (0) and Compound (9) | | | | |
|---|---|---|---|---|
| Carbon | Clausenamide (ppm) | (VII) (ppm) | (0) (ppm) | (9) (ppm) |
| 2 | 173.6 | 174.6 | 172.2 | 172.7 |
| 3 | 68.9 | 75.6 | 80.3 | 69.3 |
| 4 | 49.9 | 55.9 | 50.7 | 46.7 |
| 5 | 65.3 | 72.2 | 70.1 | 68.4 |
| 6 | 30.4 | 29.0 | 27.3 | 28.2 |
| 7 | 71.9 | 51.5 | 82.5 | 77.3 |
| 1' | 136.0 | 134.9 | 133.3 | 140.5 |
| 2' | | 143.4 | | |
| 1" | 140.5 | 141.6 | 139.1 | 141.8 |
| aromatic carbon | 126.3 | 128.9 | 125.4 | 125.9 |
| | 128.9 | 124.9 | 128.5 | 128.5 |

EXAMPLE 5

Influence of Compounds According to the Invention on Liver Functions

Male Kunming strain mice weighing 18-22 grams were used throughout the experiments. The compounds to be tested were suspended in 5% Tween 80 and given orally by gavage. The vehicle of 5% Tween 80 solution was administered to control mice via the same route. In in vitro experiments, the compounds were dissolved in dimethylformamide and added directly into the incubation mixture.

The parameters adopted for hepatotoxicity included serum transaminase (SGPT), liver triglycerides, and pathological examination of liver tissues. The liver lesions were scored mainly by the extent of inflammation and necrosis and graded from 0 to 4.

(a) Hepato-protective action

Mice were divided into 3 groups. The control group was administered the vehicle. The other groups were given two doses (250 mg/kg) of each compound at an interval of 8 h, respectively. 10 ml/kg of 0.1% CCl₄ in vegetable oil was injected ip 24 h after the second administration of the compound. The mice were fasted for 16 h and sacrificed by decapitation. SGPT and liver lipids were determined. A piece of liver was processed into sections for pathological observation.

As shown in table 9, both Clausenamide and Compound (O) significantly decreased SGPT levels of CCl₄-intoxicated mice.

(b) Protective action of Clausenamide against CCl₄, thioacetamide and acetaminophen.

The procedure of experiment of anti-CCl₄ hepatotoxicity was the same as described above. The dosages of the active compound used were 125 and 250 mg/kg. The data listed in table 10 indicate that Clausenamide at the dosage of 125 and 250 mg/kg significantly depressed the elevation of SGPT induced by CCl4. The liver injuries such as inflammation and necrosis of the mice treated with 250 mg/kg of the compound were less severe than those of the control. Liver lipids were not decreased.

In another experiment, mice were first injected 10 mg/kg of 0.15% CCl4 in vegetable oil every other day for 3 doses. Treatment of the mice with Clausenamide (250 mg/kg daily) started from the second to fifth day after the first injection of CCl4. The determination of SGPT and pathological examination of liver tissues were performed on day 7 of the experiment. The results indicate that the compound exhibited significant SGPT lowering action but had no effect on liver lesions (Table 11).

In the experiment of thioacetamide hepatotoxicity, mice were treated according to the procedure of the first experiment except that thioacetamide (50 mg/kg) was used instead of CCl4. It was found that Clausenamide markedly lowered the SGPT levels (Table 12).

The experiment of anti-acetaminophen hepatotoxicity was performed in the following way. Mice were administered two doses (250 mg/kg) of Clausenamide on the first day followed by the same dose on the second day. A dose of 150 mg/kg of acetaminophen was injected ip 6 h after the last dose of the compound. SGPT was determined and liver tissues were examined 20 h after acetaminophen injection. Clausenamide markedly decreased SGPT levels and hepatic injuries (Table 13).

(c) Effect on serum and liver transaminase (GPT) levels of normal mice

Two groups of mice were administered the vehicle or 250 mg/kg of Clausenamide once daily for 7 consecutive days, respectively. The serum and liver GPT were determined 24 h after the last dose administration. As shown in table 14, SGPT level of the mice treated with Clausenamide was slightly higher than that of the control, but the difference was not significant. Similar results were obtained for liver GPT.

(d) Induction of hepatic microsomal cytochrome P-450

The liver microsomal cytochrome P-450 plays a key role in the detoxification of xenobiotics. Mice were administered 250 mg/kg of Clausenamide once daily for 3 days. The control mice received the vehicle. The mice were killed after fasting overnight. Liver microsomes were prepared and microsomal monooxygenases were determined.

The data are shown in table 15. The hepatic cytochrome P-450, cytochrome b5, NADPH-cytochrome c reductase, aminopyrine demethylase and benzo(a)pyrene hydroxylase activities were all increased significantly.

In another experiment, mice were given a dose of 250 mg/kg of Clausenamide. Sodium pentobarbital (50 mg/kg) was injected ip 1 and 24 h after administration of the compounds. The sleeping time was estimated by recording the interval of disappearance and recovery of righting reflex. The data was listed in table 16. When Clausenamide was administered 24 h before the injection of pentobarbital, the sleeping time of mice was shortened significantly, whereas the sleeping time was prolonged markedly instead of being shortened when the compound was given 1 h prior to pentobartital injection. However, prior administration of the compound did not affect sleeping time of mice induced by barbital which is not metabolized by the liver. This means that the prolongation of pentobarbital sleeping time by Clausenamide was due to the inhibition of liver drug metabolism enzyme. Therefore, the compound has biphasic action on the hepatic microsomal cytochrome P-450 i.e., inhibition and followed by induction.

(e) Acute toxicity test:

A single dose of 3 grams/kg of Clausenamide given orally to 10 mice did not cause death in 7 days.

TABLE 9

Effect on SGPT levels of CCl4 intoxicated mice (9 per group)

| | SGPT unit % $\overline{X} \pm SE$ | P |
|---|---|---|
| Control | 1678 ± 261 | |
| Compound (0) | 391 ± 94 | <0.01 |
| Clausenamide | 617 ± 323 | <0.01 |

TABLE 10

Protective action against CCl4 hepatoxicity in mice

| Group | SGPT unit % $\overline{X} \pm SE$ | Liver lipids mg/g liver $\overline{X} \pm SE$ | Liver lesions Inflammation grade | Necrosis grade |
|---|---|---|---|---|
| Control | 3016 ± 23 | 21.0 ± 4.2 | 1.70 | 2.33 |
| Clausenamide 125 mg/kg × 2 | 2365 ± 245* | 21.6 ± 4.4 | — | — |
| 250 mg/kg × 2 | 1900 ± 257** | 13.4 ± 3.0 | 0.38 | 1.33 |

Nine mice per group.
*P < 0.05; **p < 0.01

TABLE 11

Therapeutic effect on CCl4 hepatoxicity in mice

| Group | Number of mice | SGPT unit % $\overline{X} \pm SE$ | P |
|---|---|---|---|
| Control | 8 | 2695 ± 110 | |
| Clausenamide (250 mg/kg/day × 4) | 8 | 1718 ± 224 | <0.01 |

TABLE 12

Protective action against thioacetamide hepatoxicity in mice

| Group | SGPT unit % $\overline{X} \pm SE$ | Liver lipids mg/g $\overline{X} \pm SE$ |
|---|---|---|
| Control | 1696 ± 231 | 61 ± 11.7 |
| Clausenamide (250 mg/kg × 2) | 718 ± 229* | 39 ± 3.9 |

Nine mice per group.
*P < 0.01

TABLE 13

Protective action against acetaminophen hepatoxicity in mice

| Parameter | Control | Clausenamide 250 mg/kg × 3 |
|---|---|---|
| SGPT unit % | 2778 ± 270 | 697 ± 163** |
| Liver lipids mg/g | 79 ± 13 | 82 ± 17 |
| Liver inflammation (grade) | 0.5 | 0.1 |
| Liver necrosis (grade) | 1.4 | 0 |

Nine mice per group.
**P < 0.01

TABLE 14

Effect on serum and liver transaminase (GPT) level of normal mice

| Group | SGPT unit % X ± SE | LGPT unit/100 mg X ± SE |
|---|---|---|
| Control | 217 ± 7.5 | 260 ± 11.6 |
| Clausenamide (250 mg/kg/day × 7) | 252 ± 22.1* | 292 ± 8.0* |

Eight mice per group
*P > 0.05

TABLE 15

Induction of hepatic microsomal cytochrome P-450 in mice (6 per group)

| | Control | Clausenamide 250 mg/kg /day × 3 |
|---|---|---|
| Liver weight g % | 4.0 ± 0.2 | 5.4 ± 0.2** |
| Microsomal protein mg/g liver | 6.3 ± 0.3 | 9.1 ± 0.6** |
| Cytochrome P-450 nmol/mg protein | 0.87 ± 0.07 | 1.14 ± 0.07** |
| NADPH-cytochrome c reductase, nmol cytochrome c reduced/min/mg protein | 103 ± 2.5 | 117 ± 2.5** |
| Cytochrome $b_5$ nmol/mg protein | 0.15 ± 0.01 | 0.19 ± 0.01 |
| Aminopyrine demethylase nmol HCHO/min protein | 81 ± 6.3 | 126 ± 5.2** |
| AHH nmol/min/mg protein | 2.6 ± 0.4 | 5.7 ± 0.76** |

**P 0.01

TABLE 16

Effect on barbiturates sleeping time in mice (10 per group)

| Barbiturate | Group | Interval between Compound and barbiturate | Sleeping time (min) X ± SE | P |
|---|---|---|---|---|
| Pentobarbital 50 mg/kg | Control | | 71 ± 7 | |
| | Clausenamide 250 mg/kg | 1 h | 152 ± 17 | <0.01 |
| | Clausenamide 250 mg/kg | 24 h | 46 ± 6 | <0.01 |
| Barbital 200 mg/kg | Control | | 197 ± 27 | |
| | Clausenamide 250 mg/kg | 1 h | 172 ± 13 | >0.05 |

EXAMPLE 6

Increase of Hypoxia Tolerance (Mouse) by Clausenamide

Collectives of male mice (20 g body weight) are placed in a plastic box divided into two chambers (size of the box: 15×28×40 cm corresponding to a volume of 16.8 l per bos). 20 mice are placed in each chamber. The box is perfused with a gas mixture containing 3.5% oxygen and 96.5% nitrogen. The perfusion volume is 4 l/min. The test substance and vehicle are administered orally 30 min before the test.

About 7 min after onset of perfusion with the hypoxic mixture animals die. The experiment is stopped when in the left hand chamber (control collective) three animals only show signs of respiration. The box is opened and the number of animals of the treated group still alive is counted.

The difference between the survived animals in both groups is evaluated using the $X^2$ test according to Fisher and Yates (1963) (Thomann et al. 1975).

TABLE 9

| dose (mg/kg p.o.) | surviving/total animals control | surviving/total animals Clausenamide | effect (%) |
|---|---|---|---|
| 10 | 9/60 | 19/60 | 19.6 |
| 30 | 9/60 | 31/60 | 41.1 |
| 100 | 9/60 | 40/60 | 58.8 |

Table 9 shows that the hypoxia tolerance is significantly increased by Clausenamide. A 59% increase in the survival rate at a dose of 100 mg/kg p.o. may be achieved only with very few substances (barbiturates).

EXAMPLE 7

Influence of Clausenamide on Retrograde Amnesia (Rat) Under Hypoxic Conditions

The apparatus (39 cm long, 21 cm high, and 21 cm wide) consists of two compartments, one made of translucent plastic (29 cm long) and the other one painted black (10 cm long). It has a bottom of spaced metal grids which are connected to a stimulating device delivering 1.6 mA for 20 s.

Both compartments are connected via a door which can be closed.

Male rats (100–120 g body weight) will be placed individually in the large compartment and allowed to explore both compartments for 3 min.

Thereafter the animals are placed in the small (dark) compartment, the connecting door is closed and the foot shock is delivered. After that the animals are put in an air-tight cage which is perfused by a gas mixture containing 3.8% oxygen and 96.2 % nitrogen. The animals are exposed to this hypoxic atmosphere until they exhibit gasping indicating ongoing respiratory failure (maximally 15 min).

24 hours later the rats are placed again in the bright compartment. The observation time is 3 min.

One experiment is performed in three groups of 15 animals each:
Group A: control group, not exposed to hypoxia
Group B: control group, receiving hypoxia after first training
Group C: treated animals, receiving hypoxia after first training.
Evaluation: the times the animals need to enter the dark compartment are measured in seconds.

The time difference between the two control groups is considered to be 100% (A−B=100%).

The time difference between the control group B and the treated group C is calculated in percent (C−B=X%). X is considered to be a measure for the potency of the antiamnestic effect of the substance tested.

| Clausenamide (mg/kg p.o.) | X (%) |
|---|---|
| 3 | 47 |
| 10 | 65 |
| 30 | 100 |

We claim:
1. A compound of the formula

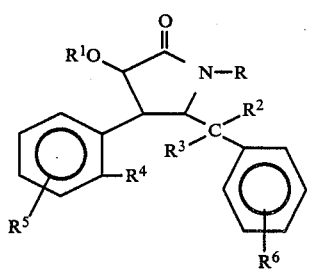

wherein

R is an alkyl, aryl or aralkyl group having from 1 to 10 carbon atoms;

R¹ represents an alkyl, aryl or aralkyl group having from 1 to 10 carbon atoms, a carboxylic acid acyl group having from 1 to 18 carbon atoms or together with R³ represents a chemical bond;

R² represents hydrogen or together with R³ represents oxygen;

R³ represents hydrogen, hydroxy, an alkoxy, aryloxy or aralkyloxy group having from 1 to 10 carbon atoms, an acyloxy group having from 1 to 18 carbon atoms, together with R¹ or R⁴ *l represents a chemical bond or together with R² represents oxygen;

R⁴ is hydrogen, together with R³ represents a chemical bond or has the meaning of R⁵; and R⁵ and R⁶ which are the same or different, represent hydrogen, an alkyl, aryl or aralkyl group having from 1 to 10 carbon atoms, an alkoxy, aryloxy or aralkoxy group having from 1 to 10 carbon atoms, a carboxylic acid acyl group having from 1 to 18 carbon atoms, CF₃, OCF₃, nitro, hydroxy, halogen, amino, dialkylamino having from 1 to 4 carbon atoms in the alkyl groups, carboxy, SO₃H or carboxylic acid acylamino having 1 to 18 carbon atoms.

2. A compound according to claim 1, wherein the alkyl and alkoxy groups contain 1 to 6 carbon atoms.

3. A compound according to claim 1, wherein the carboxylic acid acyl groups contain 1 to 4 carbon atoms.

4. A compound according to claim 1, wherein the aryl, aralkyl, aryloxy and aralkyloxy groups are phenyl, benzyl, phenoxy and benzyloxy groups, respectively.

5. A compound according to claim 1, wherein
R is methyl;
R¹ is alkyl, carboxylic acid or together with R³ is a chemical bond;
R² is hydrogen;
R³ is, alkyloxy, carboxylic acid acyloxy or together with R⁴ represents a chemical bond and
R⁵ and R⁶ are hydrogen.

6. A substantially pure stereoisomer of the formula

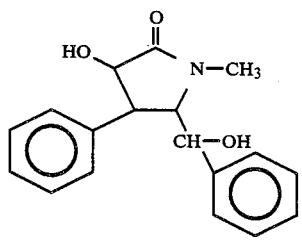

7. Substantially pure clausenamide of the formula

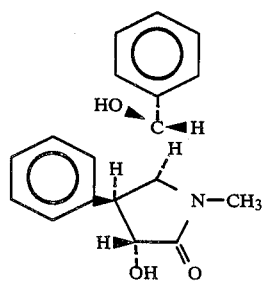

8. The substantially pure compound of the formula

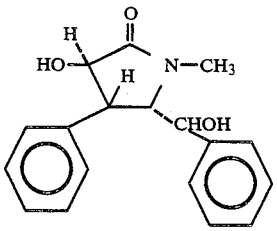

9. The substantially pure compound of the formula

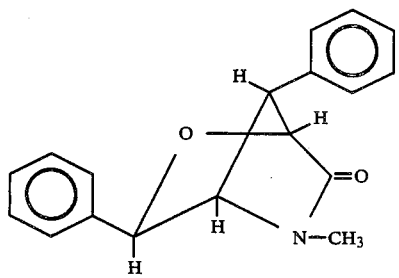

* * * * *

UNITED STATES PATENT AND TRADEMARK OFFICE
CERTIFICATE OF CORRECTION

PATENT NO. : 4,879,390

DATED : November 7, 1989

INVENTOR(S) : Chen et al

It is certified that error appears in the above-identified patent and that said Letters Patent is hereby corrected as shown below:

Col. 15, claim 1, line 23    Delete " hydroxy "

Col. 15, claim 1, line 26    Delete " $R^1$ or $R^{4\prime}$ " and substitute -- $R^4$ --

Signed and Sealed this

Thirtieth Day of July, 1991

Attest:

HARRY F. MANBECK, JR.

Attesting Officer

Commissioner of Patents and Trademarks